US007941325B2

(12) United States Patent
Heald et al.

(10) Patent No.: US 7,941,325 B2
(45) Date of Patent: May 10, 2011

(54) SYSTEM AND METHOD OF USING A NON-RETAIL CENTRAL FILLING FACILITY TO PROCESS PHARMACY PRODUCT PRESCRIPTIONS IN A PHARMACY RETAIL NETWORK

(75) Inventors: Susan Heald, Buffalo Grove, IL (US); Amylu Miller, Wauconda, IL (US); Charles Goodall, Hawthorn Woods, IL (US)

(73) Assignee: Walgreen Co., Deerfield, IL (US)

( * ) Notice: Subject to any disclaimer, the term of this patent is extended or adjusted under 35 U.S.C. 154(b) by 330 days.

(21) Appl. No.: 12/271,047

(22) Filed: Nov. 14, 2008

(65) Prior Publication Data

US 2010/0125461 A1    May 20, 2010

(51) Int. Cl.
*G06Q 10/00* (2006.01)
*G06F 19/00* (2006.01)

(52) U.S. Cl. ............................................. 705/2; 705/3
(58) Field of Classification Search .................... 705/2–3
See application file for complete search history.

(56) References Cited

U.S. PATENT DOCUMENTS

| | | | |
|---|---|---|---|
| 4,457,772 A | 7/1984 | Haynes et al. |
| 4,852,001 A | 7/1989 | Tsushima et al. |
| 5,053,970 A | 10/1991 | Kurihara et al. |
| 5,072,383 A | 12/1991 | Brimm et al. |
| 5,260,868 A | 11/1993 | Gupta et al. |
| 5,289,370 A | 2/1994 | Lirov |
| 5,337,919 A | 8/1994 | Spaulding et al. |
| 5,548,518 A | 8/1996 | Dietrich et al. |
| 5,559,710 A | 9/1996 | Shahraray et al. |
| 5,597,995 A | 1/1997 | Williams et al. |
| 5,615,121 A | 3/1997 | Babayev et al. |
| 5,619,991 A | 4/1997 | Sloane |
| 5,630,070 A | 5/1997 | Dietrich et al. |
| 5,737,539 A | 4/1998 | Edelson et al. |
| 5,737,728 A | 4/1998 | Sisley et al. |
| 5,748,907 A | 5/1998 | Crane |
| 5,758,095 A | 5/1998 | Albaum et al. |
| 5,765,139 A | 6/1998 | Bondy |
| 5,790,785 A | 8/1998 | Klug et al. |
| 5,797,515 A | 8/1998 | Liff et al. |
| 5,801,755 A | 9/1998 | Echerer |
| 5,826,236 A | 10/1998 | Narimatsu et al. |
| 5,826,252 A | 10/1998 | Wolters, Jr. et al. |
| 5,845,255 A | 12/1998 | Mayaud |

(Continued)

FOREIGN PATENT DOCUMENTS

EP    0 921 488 A1    6/1999

(Continued)

OTHER PUBLICATIONS

"The Virtual Pharmacist," *Rural Electric*, vol. 60, No. 6, Mar. 2002, p. 20.

(Continued)

*Primary Examiner* — Luke Gilligan
*Assistant Examiner* — Joseph Burgess
(74) *Attorney, Agent, or Firm* — Francis C. Kowalik; Marshall, Gerstein & Borun LLP

(57) ABSTRACT

The claimed method and system implements an algorithm for routing electronic prescriptions to one of a pharmacy retail store or a non-retail central filling facility for physical preparation of pharmacy products corresponding to the electronic prescriptions.

20 Claims, 11 Drawing Sheets

U.S. PATENT DOCUMENTS

| | | | |
|---|---|---|---|
| 5,852,259 | A | 12/1998 | Yanase et al. |
| 5,907,493 | A | 5/1999 | Boyer et al. |
| 5,911,687 | A | 6/1999 | Sato et al. |
| 5,915,240 | A | 6/1999 | Karpf |
| 5,924,074 | A | 7/1999 | Evans |
| 5,946,883 | A | 9/1999 | Yuyama et al. |
| 5,954,640 | A | 9/1999 | Szabo |
| 5,963,911 | A | 10/1999 | Walker et al. |
| 5,970,462 | A | 10/1999 | Reichert |
| 5,987,519 | A | 11/1999 | Peifer et al. |
| 6,067,524 | A | 5/2000 | Byerly et al. |
| 6,078,912 | A | 6/2000 | Buerger et al. |
| 6,112,182 | A | 8/2000 | Akers et al. |
| 6,202,080 | B1 | 3/2001 | Lu et al. |
| 6,202,923 | B1 | 3/2001 | Boyer et al. |
| 6,208,973 | B1 | 3/2001 | Boyer et al. |
| 6,256,550 | B1 | 7/2001 | Wu et al. |
| 6,266,655 | B1 | 7/2001 | Kalyan |
| 6,294,999 | B1 | 9/2001 | Yarin et al. |
| 6,311,163 | B1 | 10/2001 | Sheehan et al. |
| 6,330,491 | B1 | 12/2001 | Lion |
| 6,347,329 | B1 | 2/2002 | Evans |
| 6,364,517 | B1 | 4/2002 | Yuyama et al. |
| 6,370,841 | B1 | 4/2002 | Chudy et al. |
| 6,381,577 | B1 | 4/2002 | Brown |
| 6,397,190 | B1 | 5/2002 | Goetz |
| 6,421,650 | B1 | 7/2002 | Goetz et al. |
| 6,438,451 | B1 | 8/2002 | Lion |
| 6,463,417 | B1 | 10/2002 | Schoenberg |
| 6,464,142 | B1 | 10/2002 | Denenberg et al. |
| 6,477,442 | B1 | 11/2002 | Valerino, Sr. |
| 6,493,427 | B1 | 12/2002 | Kobylevsky et al. |
| 6,496,427 | B2 | 12/2002 | Kojima et al. |
| 6,523,009 | B1 | 2/2003 | Wilkins |
| 6,539,281 | B2 | 3/2003 | Wan et al. |
| 6,564,121 | B1 | 5/2003 | Wallace et al. |
| 6,625,952 | B1 | 9/2003 | Chudy et al. |
| 6,665,740 | B1 | 12/2003 | Mason, Jr. et al. |
| 6,711,460 | B1 | 3/2004 | Reese |
| 6,735,497 | B2 | 5/2004 | Wallace et al. |
| 6,741,724 | B1 | 5/2004 | Bruce et al. |
| 6,874,684 | B1 | 4/2005 | Denenberg et al. |
| 6,947,900 | B2 | 9/2005 | Giordano, III et al. |
| 7,058,584 | B2 | 6/2006 | Kosinski et al. |
| 7,111,780 | B2 | 9/2006 | Broussard et al. |
| 7,139,639 | B2 | 11/2006 | Broussard et al. |
| 2001/0009005 | A1 | 7/2001 | Godin et al. |
| 2002/0019786 | A1 | 2/2002 | Gonzalez et al. |
| 2002/0052770 | A1 | 5/2002 | Podrazhansky |
| 2002/0062175 | A1 | 5/2002 | Lion |
| 2002/0062230 | A1 | 5/2002 | Morag et al. |
| 2002/0120573 | A1 | 8/2002 | McCormick |
| 2002/0153411 | A1 | 10/2002 | Wan et al. |
| 2002/0188467 | A1 | 12/2002 | Eke |
| 2002/0198454 | A1 | 12/2002 | Seward et al. |
| 2003/0074234 | A1 | 4/2003 | Stasny |
| 2003/0109950 | A1 | 6/2003 | Andrade et al. |
| 2003/0149599 | A1 | 8/2003 | Goodall et al. |
| 2003/0179287 | A1 | 9/2003 | Kozic et al. |
| 2003/0225595 | A1* | 12/2003 | Helmus et al. .................... 705/2 |
| 2004/0019794 | A1* | 1/2004 | Moradi et al. ................. 713/185 |
| 2004/0117046 | A1 | 6/2004 | Colle et al. |
| 2004/0133705 | A1 | 7/2004 | Broussard et al. |
| 2004/0172289 | A1 | 9/2004 | Kozic et al. |
| 2004/0220829 | A1 | 11/2004 | Baharav et al. |
| 2004/0221034 | A1 | 11/2004 | Kausik et al. |
| 2004/0260577 | A1 | 12/2004 | Dahlin et al. |
| 2005/0075902 | A1 | 4/2005 | Wager et al. |
| 2005/0125798 | A1 | 6/2005 | Peterson |
| 2006/0041330 | A1 | 2/2006 | Ansari et al. |
| 2006/0149587 | A1* | 7/2006 | Hill et al. .......................... 705/2 |
| 2006/0276933 | A1 | 12/2006 | Chavez et al. |
| 2006/0287906 | A1 | 12/2006 | McGillin |

FOREIGN PATENT DOCUMENTS

| | | |
|---|---|---|
| JP | 361217880 A | 9/1986 |
| WO | WO-96/13790 A1 | 5/1996 |
| WO | WO-01/08393 A1 | 2/2001 |

OTHER PUBLICATIONS

"CVS, Merck-Medco in E-commerce Alliance," Chain Drug Review, 21(18):2 (1999).

Colchamiro "Independents Look to Go Online," American Druggist, Sep. 1999, pp. 1-3.

McNaughton, "Can Net Drugstores Outpace the Chains?" CNET News.com, Feb. 24, 1999, 1 page.

Walgreens On-line Prefills (Website Printout Packet-printed Jul. 5, 2006) archived as Jun. 17, 1998, p. 1-13.

Wolvorton, "Online Pharmacies Partner for Power," CNET News.com, Oct. 8, 1999, pp. 1-2.

"Name Change Reflects CVS' Commitment to E-commerce," *Chain Drug Review*, 21(15):2 (1999).

"Optimize your Enterprise for Maximum Profitability," NDCHEALTH, May 5, 2005, 4 pages.

"File Locking," www.wikipedia.org/wili/file_locking obtained via web.archive.com.

Office Action issued in U.S. Appl. No. 11/252,776 dated Sep. 28, 2009.

Office Action issued in U.S. Appl. No. 11/252,947 dated Sep. 2, 2009.

Office Action issued in U.S. Appl. No. 11/253,096 dated Jun. 10, 2009.

Office Action issued in U.S. Appl. No. 11/253,253 dated Jul. 20, 2009.

Final Office Action issued in U.S. Appl. No. 11/252,775 dated Sep. 29, 2009.

Final Office Action issued in U.S. Appl. No. 11/252,759 dated Jan. 15, 2010.

Final Office Action issued in U.S. Appl. No. 11/253,185 dated Jan. 8, 2010.

Office Action issued in U.S. Appl. No. 11/253,252 dated Sep. 3, 2009.

Final Office action for U.S. Appl. No. 11/252,947 dated Oct. 4, 2010.

Office action for U.S. Appl. No. 12/248,774 dated Oct. 28, 2010.

Office action for U.S. Appl. No. 11/252,759 dated Aug. 6, 2010.

Office action for U.S. Appl. No. 11/252,947 dated Mar. 17, 2010.

Final Office action for U.S. Appl. No. 11/253,252 dated Mar. 5, 2010.

Final Office action for U.S. Appl. No. 11/252,776 dated Apr. 22, 2010.

Final Office action for U.S. Appl. No. 11/253,253 dated Mar. 9, 2010.

* cited by examiner

SYSTEM AND METHOD OF USING A NON-RETAIL CENTRAL FILLING FACILITY TO PROCESS PHARMACY PRODUCT PRESCRIPTIONS IN A PHARMACY RETAIL NETWORK

TECHNICAL FIELD

The present invention generally relates to a process and system for managing pharmacy product prescription filling in a pharmacy network.

BACKGROUND

Pharmacy prescription products may generally be processed completely by a single pharmacy retail store that receives a paper prescription, conditions the prescription information for filling, physically prepares a set of pharmacy products for the prescription, and releases the pharmacy products to a customer. Generally, a local pharmacist at the pharmacy retail store may be involved in some or all of the physical filling process. However, pharmacist time may be better spent outside of physical preparation of a pharmacy product. For example, pharmacist time may be more efficiently spent in an advisory role to a customer to educate patients/customers about their prescriptions. Moreover, in a pharmacy company that controls a plurality of pharmacy retail stores, physical preparation of pharmacy products may be more efficiently performed by a central facility to take advantage of economies of scale with respect to service personnel and equipment.

SUMMARY

The method and system makes pharmacy prescription orders available over a communication network that connects a plurality of pharmacy resources (e.g., pharmacy retail stores and non-retail facilities) and selectively routes a pharmacy product prescription order to a non-retail central filling facility or a pharmacy retail store for physical preparation of a pharmacy product corresponding to the pharmacy prescription order. The routing may be performed based on a set of parameters that include a pickup time of an electronic prescription order, an inventory level of a pharmacy product at a pharmacy retail store, an inventory level of a pharmacy product at a central filling facility, prescription type exceptions, etc. In one embodiment, two or more central filling facilities may be used in the pharmacy system and routing of prescription orders may involve routing prescription orders between the first central filling facility and the second central filling facility based on the respective workloads of the central filling facilities.

DETAILED DESCRIPTION

Although the following text sets forth a detailed description of numerous different embodiments, it should be understood that the legal scope of the invention is defined by the words of the claims set forth at the end of this patent. The detailed description is to be construed as exemplary only and does not describe every possible embodiment since describing every possible embodiment would be impractical, if not impossible. Numerous alternative embodiments could be implemented, using either current technology or technology developed after the filing date of this patent, which would still fall within the scope of the claims.

It should also be understood that, unless a term is expressly defined in this patent using the sentence "As used herein, the term '_____' is hereby defined to mean . . . " or a similar sentence, there is no intent to limit the meaning of that term, either expressly or by implication, beyond its plain or ordinary meaning, and such term should not be interpreted to be limited in scope based on any statement made in any section of this patent (other than the language of the claims). To the extent that any term recited in the claims at the end of this patent is referred to in this patent in a manner consistent with a single meaning, that is done for sake of clarity only so as to not confuse the reader, and it is not intended that such claim term be limited, by implication or otherwise, to that single meaning. Finally, unless a claim element is defined by reciting the word "means" and a function without the recital of any structure, it is not intended that the scope of any claim element be interpreted based on the application of 35 U.S.C. §112, sixth paragraph.

Figure 1:
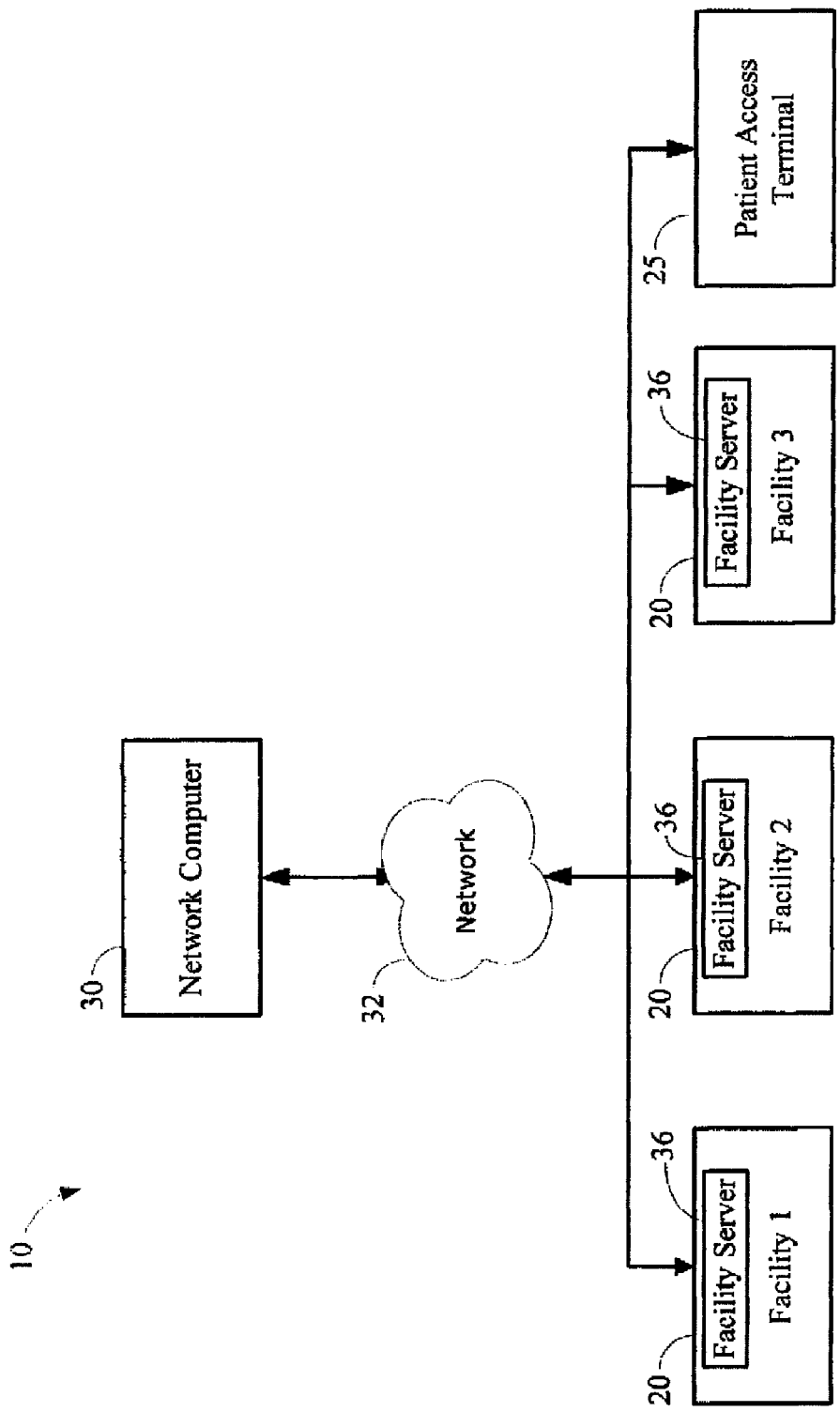
FIGS. 1-3 illustrate block diagrams of a computing system that may operate in accordance with the described embodiments.

FIG. 1 illustrates an embodiment of a data network 10 including a first group of pharmacies 20 operatively coupled to a network computer 30 via a network 32. The plurality of pharmacies 20 may be located, by way of example rather than limitation, in separate geographic locations from each other, in different areas of the same city, or in different states. The network 32 may be provided using a wide variety of techniques well known to those skilled in the art for the transfer of electronic data. For example, the network 32 may comprise dedicated access lines, plain ordinary telephone lines, satellite links, combinations of these, etc. Additionally, the network 32 may include a plurality of network computers or server computers (not shown), each of which may be operatively interconnected in a known manner. Where the network 32 comprises the Internet, data communication may take place over the network 32 via an Internet communication protocol.

The network computer 30 may be a server computer of the type commonly employed in networking solutions. The network computer 30 may be used to accumulate, analyze, and download pharmacy data. For example, the network computer 30 may periodically receive data from each of the pharmacies 20 indicative of information pertaining to a prescription order, billing information, employee data, etc. The pharmacies 20 may include one or more facility servers 36 that may be utilized to store information for a plurality of customers/employees/accounts/etc. associated with each facility.

Although the data network 10 is shown to include one network computer 30 and three pharmacies 20, it should be understood that different numbers of computers and pharmacies may be utilized. For example, the network 32 may include a plurality of network computers 30 and dozens of pharmacies 20, all of which may be interconnected via the network 32. According to the disclosed example, this configuration may provide several advantages, such as, for example, enabling near real time uploads and downloads of information as well as periodic uploads and downloads of information. This provides for a primary backup of all the information generated in the process of updating and accumulating pharmacy data.

Figure 2:
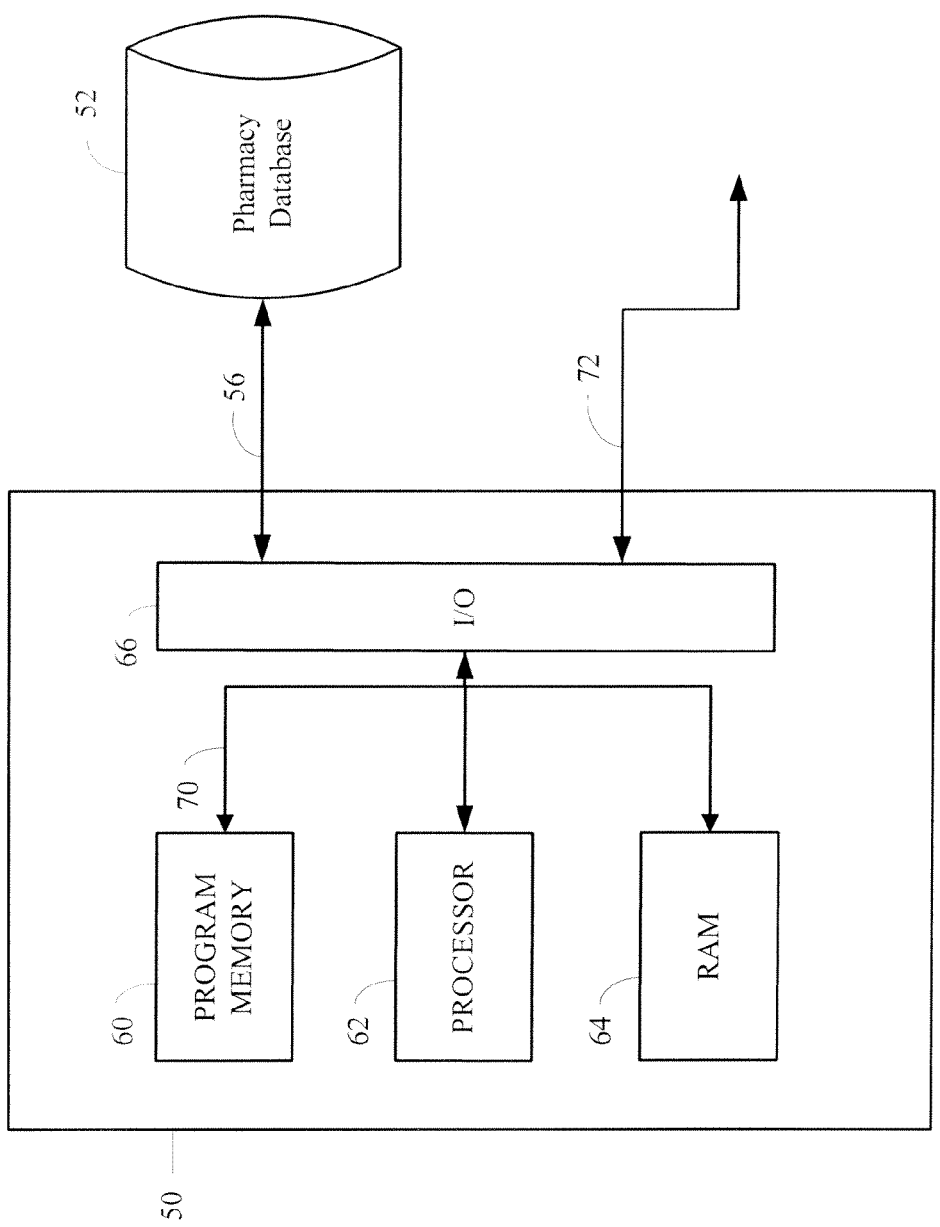

FIG. 2 is a schematic diagram of one possible embodiment of the network computer 30 shown in FIG. 1. The network computer 30 may have a controller 50 that is operatively connected to a database 52 via a link 56. It should be noted that, while not shown, additional databases may be linked to the controller 50 in a known manner.

The controller 50 may include a program memory 60, a microcontroller or a microprocessor (MP) 62, a random-access memory (RAM) 64, and an input/output (I/O) circuit 66, all of which may be interconnected via an address/data bus 70. It should be appreciated that although only one microprocessor 62 is shown, the controller 50 may include multiple microprocessors 62. Similarly, the memory of the controller 50 may include multiple RAMs 64 and multiple program memories 60. Although the I/O circuit 66 is shown as a single block, it should be appreciated that the I/O circuit 66 may include a number of different types of I/O circuits. The RAM(s) 64 and programs memories 60 may be implemented as semiconductor memories, magnetically readable memories, and/or optically readable memories, for example. The controller 50 may also be operatively connected to the network 32 via a link 72.

Figure 3:
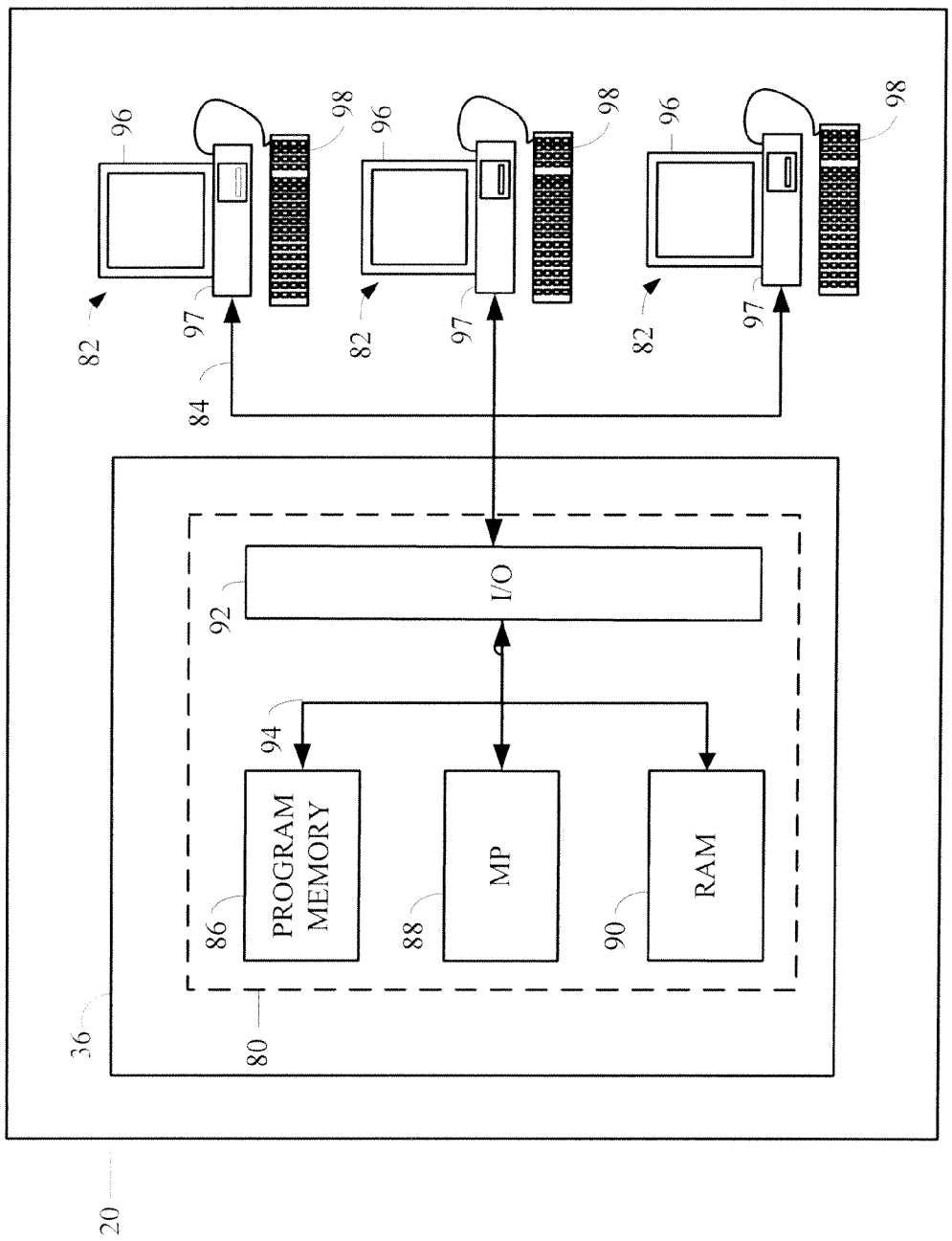

FIG. 3 is a schematic diagram of one possible embodiment of several components located in one or more of the pharmacies 20 from FIG. 1. Although the following description addresses the design of the pharmacies 20, it should be understood that the design of one or more of the pharmacies 20 may be different than the design of other pharmacies 20. Also, each pharmacy 20 may have various different structures and methods of operation. It should also be understood that the embodiment shown in FIG. 3 illustrates some of the components and data connections present in a pharmacy, however it does not illustrate all of the data connections present in a typical pharmacy. For exemplary purposes, one design of a pharmacy is described below, but it should be understood that numerous other designs may be utilized.

The pharmacies 20 may have a facility server 36, which includes a controller 80, wherein the facility server 36 is operatively connected to a plurality of client device terminals 82 via a network 84. The network 84 may be a wide area network (WAN), a local area network (LAN), or any other type of network readily known to those persons skilled in the art. The client device terminals 82 may also be operatively connected to the network computer 30 from FIG. 1 via the network 32.

Similar to the controller 50 from FIG. 2, the controller 80 may include a program memory 86, a microcontroller or a microprocessor (MP) 88, a random-access memory (RAM) 90, and an input/output (I/O) circuit 92, all of which may be interconnected via an address/data bus 94. As discussed with reference to the controller 50, it should be appreciated that although only one microprocessor 88 is shown, the controller 80 may include multiple microprocessors 88. Similarly, the memory of the controller 80 may include multiple RAMs 90 and multiple programs memories 86. Although the P/O circuit 92 is shown as a single block, the I/O circuit 92 may include a number of different types of I/O circuits. The RAM(s) 90 and program memories 86 may also be implemented as semiconductor memories, magnetically readable memories, and/or optically readable memories, for example.

The client device terminals 82 may include a display 96, a controller 97, a keyboard 98 as well as a variety of other input/output devices (not shown) such as a scanner, printer, mouse, touch screen, track pad, track ball, isopoint, voice recognition system, scale, digital camera, etc. Each client device terminal 82 may be signed onto and occupied by a pharmacy employee to assist them in performing their duties. Pharmacy employees may sign onto a client device terminal 82 using any generically available technique, such as entering a user name and password. If a pharmacy employee is required to sign onto a client device terminal 82, this information may be passed via the link 84 to the facility server 36, so that the controller 80 will be able to identify which pharmacy employees are signed onto the system and which client device terminals 82 the employees are signed onto. This may be useful in monitoring the pharmacy employees' productivity.

Typically, facility servers 36 store a plurality of files, programs, and other data for use by the client device terminals 82 and the network computer 30. One facility server 36 may handle requests for data from a large number of client device terminals 82. Accordingly, each facility server 36 may typically comprise a high end computer with a large storage capacity, one or more fast microprocessors, and one or more high speed network connections. Conversely, relative to a typical facility server 36, each client device terminal 82 may typically include less storage capacity, a single microprocessor, and a single network connection.

Generally, a pharmacy retail store provides an interface to customers for interacting with the pharmacy retail network including the services offered by the pharmacy retail network. Consequently, pharmacy retail store personnel such as pharmacists and technicians may be involved in a number of different activities including operational activities (such as prescription processing) and customer relationship management activities. This division of pharmacist and non-pharmacist (i.e., technician) time may reduce the retail store efficiency in filling pharmacy prescription orders while at the same time reduce the effectiveness of the customer relationship activities.

Moreover, various equipment may be used in physical filling of a pharmacy prescription product, where the equipment may be more efficiently operated when applied to aggregated bulk orders. Generally, the equipment may be inefficiently used due to the inability to properly match the workload of a particular pharmacy with the capacity of the equipment. Thus, the equipment may often be underutilized.

In a pharmacy company that controls a plurality of pharmacy retail stores, physical preparation of pharmacy products may be more efficiently performed by a central facility to take advantage of economies of scale with respect to service personnel and equipment.

A central filling facility may be a non-retail pharmacy resource that is designed to primarily perform physical filling of a received electronic pharmacy prescription order. In one embodiment, the central filling facility may receive a fill-ready, information processed prescription order that primarily requires physical filling to complete the order process. The central filling facility may perform the processes generally needed to physically prepare a pharmacy product corresponding to a prescription. This may include operating equipment, managing supplies, etc. necessary to physically prepare a type and quantity of pharmacy product corresponding to a prescription. In one embodiment, a non-retail prescription filling facility does not physically release a filled prescription order (e.g., a set of pharmacy products prepared based on the prescription) to a customer. In this embodiment, the central filling facility may not provide physical interaction with a customer. In one embodiment, a pharmacy retail network may include a plurality of central filling facilities. For example, the central filling facilities may be disposed regionally and be assigned to handle work of a region.

The central prescription filling facility may be staffed to include a set of registered pharmacists and/or non-registered pharmacists (also called technicians) that perform the physical filling of prescriptions. The central filling facility may include equipment necessary to fill a set of pharmacy products. In one embodiment, the central filling facility may be configured to house and operate bulk filling equipment that provides reductions in cost (e.g., labor cost) when applied to large volume fills. This bulk filling equipment may provide cost savings over individual filling efforts at a pharmacy retail store. For example, various bulk dispensing and repackaging equipment may be used in the central filling facility where this equipment may not be practical in a pharmacy retail store that operates with smaller volumes of prescriptions. Using bulk filling equipment at a central filling facility to aggregate prescription orders and process them in bulk may form another advantage of including a central filling facility in a pharmacy retail network.

Figure 4:
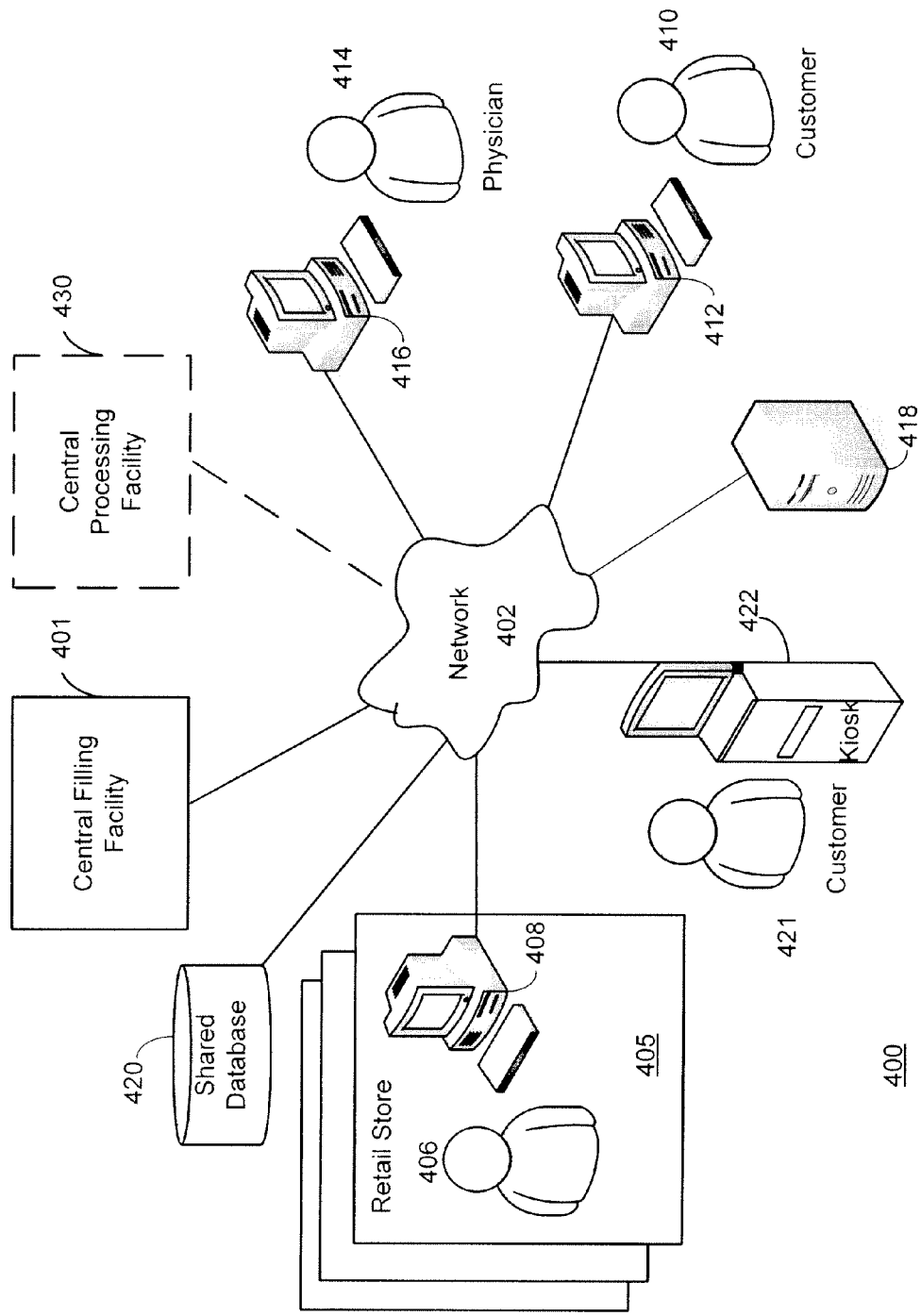
FIG. 4 illustrates a general system embodiment of a pharmacy retail network including pharmacy retail stores and non-retail facilities such as a central filling facility.

FIG. 4 illustrates an embodiment of a pharmacy retail system 400 using a non-retail, central filling facility 401. Generally, a network 402 may be used to communicatively couple different computers associated with different entities of a pharmacy retail network. The pharmacy computing system 400 may correspond to a pharmacy retail network including a plurality of pharmacy resources. Pharmacy resources may include retail resources, such as pharmacy retail stores 405 and non-retail resources, such as the central filling facility 401. The pharmacy retail system may also include a central non-retail information processing facility 430 (discussed further below).

The network 402 may be completely controlled (e.g., owned) by the pharmacy retail network or may be partially owned and controlled by the pharmacy retail network. For example, a portion of the network 402 may be a private network that is controlled by the pharmacy retail network and a portion of the network may be coupled to the Internet. In one embodiment, a customer may visit a pharmacy retail store 405 to originate a prescription order. In this embodiment, the customer may interact with pharmacy personnel 406 (pharmacist, technician, etc.) to originate a prescription using a pharmacy retail store computer 408.

In some embodiments, a customer 410 may use a computer 412 to connect to the network 402 when originating and sending a raw prescription order for processing. Similarly, a physician 414 may use a computer 416 to connect to the network 402 when originating a raw prescription for a patient and sending the raw prescription order for processing. The customer computer 412 and physician computer 416 may communicate with the pharmacy retail system 400 via an Internet connection (that is not owned by the pharmacy retail network).

In some embodiments, a customer 421 may use a kiosk 422 to originate a prescription order. In one embodiment the kiosk may be communicatively coupled to a private portion of the network 402. In another embodiment, the kiosk 422 may also connect to the network 402 via a public Internet portion of network 402. FIG. 4 further illustrates a database 420 and a server 418 that may be used to facilitate prescription order processing across the pharmacy retail system 400.

Figure 5:
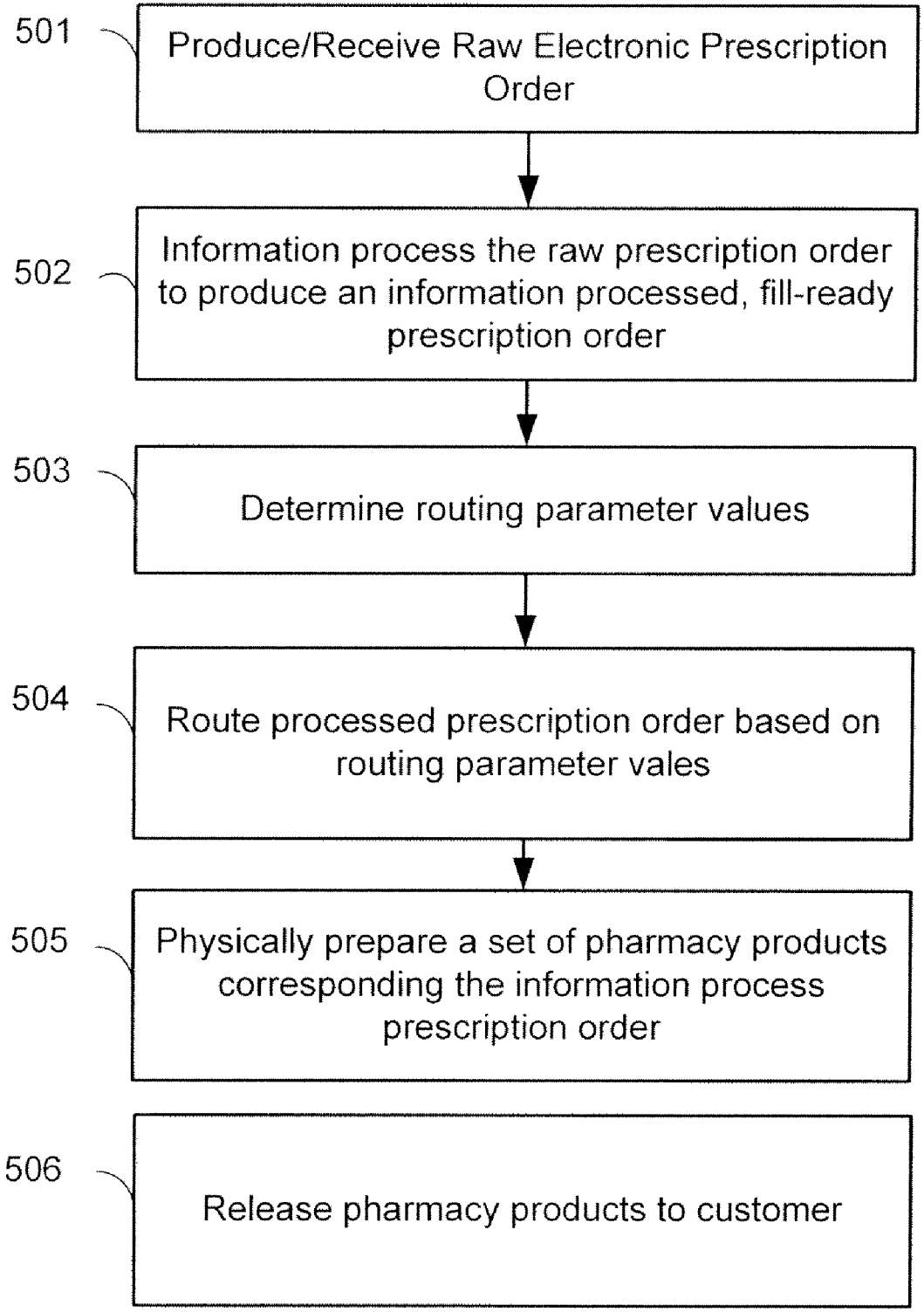
FIG. 5 illustrates an exemplary embodiment for selectively routing a prescription order to a central filling facility or a pharmacy retail store for physical filling of pharmacy products corresponding to the prescription order.

FIG. 5 illustrates an exemplary embodiment for selectively routing a prescription order to a central filing facility or a pharmacy retail store for physical filling of pharmacy products corresponding to the prescription order. In this embodiment, a raw electronic prescription order may be originated or generated (block 501). For example, a raw electronic prescription order may be originated at a pharmacy retail store, at a kiosk, at a customer terminal, at a physician terminal, etc. In some embodiments of the system that include a central information processing facility 431, a raw electronic prescription order may be taken over a phone by a representative at the central processing facility 431 and originated at the central processing facility 431.

At block 502, the raw electronic prescription order may be information processed to produce an information processed, fill-ready prescription order. Information processing the raw electronic prescription order may include multiple processes that condition the information in the raw electronic prescription to produce a prescription for physical filling. The information processing may be performed at a pharmacy retail store 405 or at a central processing facility 430, as described in a related U.S. patent application Ser. No. 12/248,774 filed on Oct. 9, 2008 and entitled "System and Method of Information Processing of Raw Pharmacy Product Prescription in a Pharmacy Retail Network," which is incorporated by reference herein.

At block 503, various routing parameters or factors may be calculated or determined. The processed, fill-ready prescription order may then be routed based on the values of these parameters at (block 504). The parameters may include a pickup time of the electronic prescription order, an inventory level of the pharmacy product at the retail store, and an inventory level of the pharmacy product at the central fill facility.

In some embodiments, a pickup time may be a time which an entity of a pharmacy network (e.g., a pharmacy retail store) has indicated to a customer that the customer prescription may be ready for release or delivery to the customer. In some embodiments, if the difference between a current time and the pickup time is less than the time necessary for preparation at and delivery by the central filling facility of a set of pharmacy products corresponding to an electronic prescription order, then the electronic prescription order may remain or be routed to a pharmacy retail store for physical filling and preparation. If the difference between a current time and the pickup time is equal to or more than the time necessary to prepare at and deliver by the central filling facility the set of pharmacy products, then the electronic prescription may be routed to the central filling facility.

In some embodiments, the time necessary to prepare the pharmacy product and or the delivery time may be calculated as an average time for physical filling of the set of pharmacy products in addition to an acceptable tolerance or difference from the average time. The tolerance level may be based on a statistically accepted threshold (e.g., standard deviation, a variance, etc.). It should be noted that delivery times may be particular to a pharmacy retail store because distances between the pharmacy retail store and the central filling facility may vary and delivery schedule may vary.

In some embodiments, an inventory level at a pharmacy retail store of a pharmacy product of the prescription may be determined as a routing parameter. For example, in situations where the product is to be released to a customer at a pharmacy retail store, the inventory level of the pharmacy product at that pharmacy retail store may be determined. In some embodiments, if the inventory level at the pharmacy retail store for the pharmacy product is insufficient to fill the prescription, then the information processed, fill-ready prescription may be routed to a central filling facility. In this embodiment, it may be assumed that the central filling facility ("central fill") generally has the pharmacy product in stock. In situations where the central fill does not currently have the necessary quantity for a pharmacy product of a prescription, the central fill may be responsible for ordering additional quantities. In such situations, there may be an unavoidable delay in preparing the prescription order for delivery to a customer and in these situations a more efficient process may be to route the prescription to the central fill to take advantage of the bulk filling processes and economies of scale.

In some embodiments, the inventory level of a pharmacy retail store and the central fill may be determined as a routing parameter. The prescription may be routed to the pharmacy retail store or the central fill based on whether the quantity of the pharmacy product is available at one or the other location. In some embodiments, if both the pharmacy retail store and the central fill have the pharmacy product quantity in stock, then other factors or parameters may be used to route the prescription (e.g., pickup time). If inventories of both the pharmacy retail store and central fill are insufficient, the prescription may be routed to the central fill facility for eventual filling (e.g., when an order of inventory is received).

In some embodiments, an inventory of a pharmacy retail store may have only a portion of the quantity necessary to fill a pharmacy product prescription. In this situation, the prescription may be routed to the pharmacy retail store for a partial fill. For example, a portion of the quantity of the prescription may be physically prepared at the pharmacy retail store for release to the customer. The prescription may then be routed to the central filling facility for preparation of a remaining portion of the prescription. This situation may occur for emergency medications, a quantity of which needs to be filled immediately. In one embodiment a priority parameter may be associated with the prescription to indicate priority prescription products. Thus, a priority may be an additional parameter to be determined when routing the electronic prescription order. It should be noted that the priority parameter may be used to indicate other priority variables such as favored customer status.

In some embodiments, routing of the electronic prescription may be based on determining the marginal cost of filling the physical prescription at the central filling facility and at a pharmacy retail store. The electronic prescription may be routed to the central filling facility when the marginal cost of filling the physical prescription at the central filling facility is less than the marginal cost of filling the physical prescription at the pharmacy retail store. In this manner, economies of scale of the central filling facility may be utilized. As discussed above, this marginal cost may be lower at a central filling facility that includes the equipment and critical volume of service personnel (e.g., dedicated pharmacists and technicians) to make it effectively cheaper to process large volumes of pharmacy products. One method of determining the marginal cost may be to use software to calculate marginal costs from supply chain monitoring data.

Based on the determined parameters at block 503, the electronic prescription may be routed to the central filling facility or a pharmacy retail store in block 504. Physical preparation of the prescription order may then begin at block 505 followed by release of the prepared prescription products to a customer at block 506.

Determining routing parameters (block 503) and selectively routing the processed prescriptions (block 504) may be performed by a number of entities within the pharmacy retail network of FIG. 4. In one embodiment, the routing may be performed at an origin of the prescription order. For example, where the prescription is originated at a pharmacy retail store, a computer of the pharmacy retail store may determine the routing parameters and route an electronic prescription accordingly. In another example, the parameter determination and selective routing may be performed at a non-retail, prescription information processing facility 430 that is dedicated to information processing raw electronic prescriptions. In one embodiment, the pharmacy network may have a designated computer act as a server which receives information processed prescription orders, determines the routing parameters, and selectively routes the prescriptions to a retail store or non-retail filling center. The designated computer may be a computer of a pharmacy retail store of the pharmacy network or the designated computer may be a designated server, such as server 418 of FIG. 4, that is not associated with one particular store (e.g., the designated computer may be housed at a non-retail, corporate headquarter or server farm).

Figure 6:
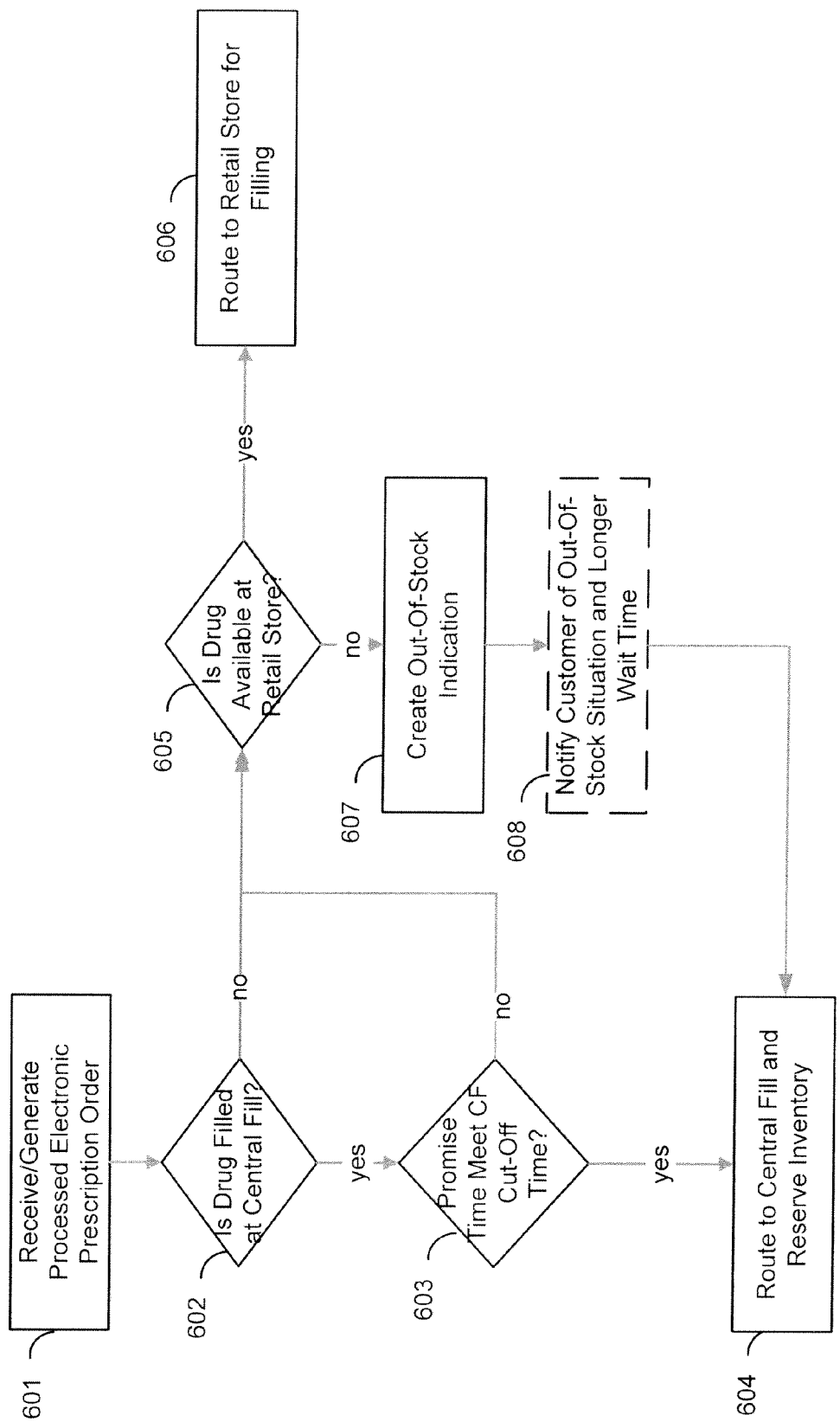
FIG. 6 illustrates a possible flow diagram of a routing process that considers multiple routing parameters including inventory and pickup time parameters.

FIG. 6 illustrates a possible flow diagram of a routing process that considers multiple routing parameters including inventory and pickup time parameters. This process may be implemented as an algorithm for execution by a computer such as computer 30 of FIG. 2. An information processed electronic prescription order may be generated in the pharmacy retail network (block 601). The process may determine whether a pharmacy product (e.g., drug or medication) is normally filled or designated to be filled at the central filling facility (block 602). In this embodiment, the central filling facility may not be configured to physically prepare every pharmacy product that is offered to customers at the pharmacy retail store. In other words, in this embodiment, there may be a set of pharmacy products that are designated to be primarily filled at a pharmacy retail store. In an alternative embodiment, the central filling facility may be assigned to primarily fill only a subset of the total number of pharmacy products offered by the pharmacy retail store, even though the central filling facility is capable of filling each pharmacy product offered.

If the pharmacy product is filled at the central filling facility, then a pickup time for the prescription may be checked to determine if the pickup time may be met with respect to a cut-off time of the central filling facility (block 603) and delivery schedule. In this embodiment, the central filling facility may prepare a pharmacy product and deliver the product at a particular frequency (e.g., once a day, twice a day, etc.). In this situation, the cutoff time for the central filling facility may determine whether a product may be prepared and ready for delivery from the central filling facility by the next delivery time. In one example, the central fill may have a cutoff time of 19:15. All prescription orders received by 19:15 may be assumed to be prepared and delivered to a pharmacy retail store by 12:00 noon of the following day. The 12:00 noon time may represent an expected delivery time. Thus, if an information processed prescription is received at a time before 19:15 and the pickup time for the prescription is after 12:00 noon the following day, then the pickup time may be met by the central filling facility. If the current time is after 19:15, then the pharmacy product may not be delivered till 12:00 noon of the day after tomorrow.

Thus, in block 603, if the pickup time is met by the central fill cutoff time (based on a current time of receipt of the prescription), then the processed prescription may be routed to the central fill (block 604). If the pickup time is not met by the central fill cutoff time, then the computing system may be determined whether or not a designated or selected pharmacy retail store has inventory of the material for preparing the pharmacy product (block 605).

Also, if at block 602, the pharmacy product is not designated for central fill or the pharmacy product is not normally prepared at central fill, then the computing system may determine whether a designated or selected pharmacy retail store has inventory of the material for preparing the pharmacy product (block 605). If the inventory of the pharmacy product is available and sufficient for the prescription order at the pharmacy retail store, then the prescription may be routed to the pharmacy retail store for physical filling (block 606).

If the inventory of the pharmacy retail store is insufficient for filling the prescription, an out of stock indication for the pharmacy product may be generated (block 607). Optionally, a customer may be notified that a pharmacy product of the customer prescription cannot be currently filled due to insufficient inventory and that a longer wait time may be incurred (block 608). The prescription order may then be routed to the central filling facility for processing (block 604).

In some embodiments, before the prescription order may be routed to the central fill 604 or retail store 606, a portion of inventory required to fill the prescription order may be reserved. This may be done by associating an appropriate indicator to an inventory database or other inventory tracking system. In this manner, a more accurate inventory count may be obtained, for example, during block 605 which may be configured to check inventory levels that do not include the reserved quantities.

In some embodiments, the pharmacy retail computing system may be configured to update or modify a prescription to indicate its filling source or location (e.g., at 604, 605, or 606). This may be performed to facilitate a return process. For example, in some embodiments, a prepared prescription that is prepared at a pharmacy location or delivered to a pharmacy (from the central filling facility) may need to be returned. This may happen when a customer does not pick up the prescription, the prescription is canceled, or when the prescription is not released to a customer by an expiration date of a prescription product. In these cases, the filling prescription may be returned to physical inventory at the pharmacy retail store or central fill (e.g., based on an indication of a filling location for the prescription product).

As discussed above, even when the central fill does not have current inventory sufficient for a prescription, the central fill may be the designated filling entity for prescriptions because the central fill may be responsible for ordering additional inventory and it may be more convenient to fill the backorder from the central fill. Thus, if the inventory is available at the central fill, then the prescription may be filled in the normal course of operation of the central fill. If the inventory is not available, then the central filling facility may generate an order for additional inventory and reserve a certain portion of that order for the prescription that prompted the order generation.

In some embodiments, the central filling facility may be integrated with a central warehousing and storage facility that distributes stock inventory of material to individual pharmacy retail stores of the pharmacy network.

In an embodiment where the central fill is assigned to fill only a subset of the total pharmacy products offered by the pharmacy network, the prescription may be routed to the central filling facility (block 604) even though a pharmacy product of the prescription is not generally processed by the central filling facility. In this situation, the routing to the central fill may be viewed as an exception handling process where a pharmacy retail store originally assigned to process the product is not able to process the pharmacy product due to low inventory.

In another embodiment, the central filling facility may simply act as a warehouse in which the necessary inventory items for filling the pharmacy product are delivered to the pharmacy retail store, which still prepares the product upon receiving the necessary inventory items.

Figure 7:
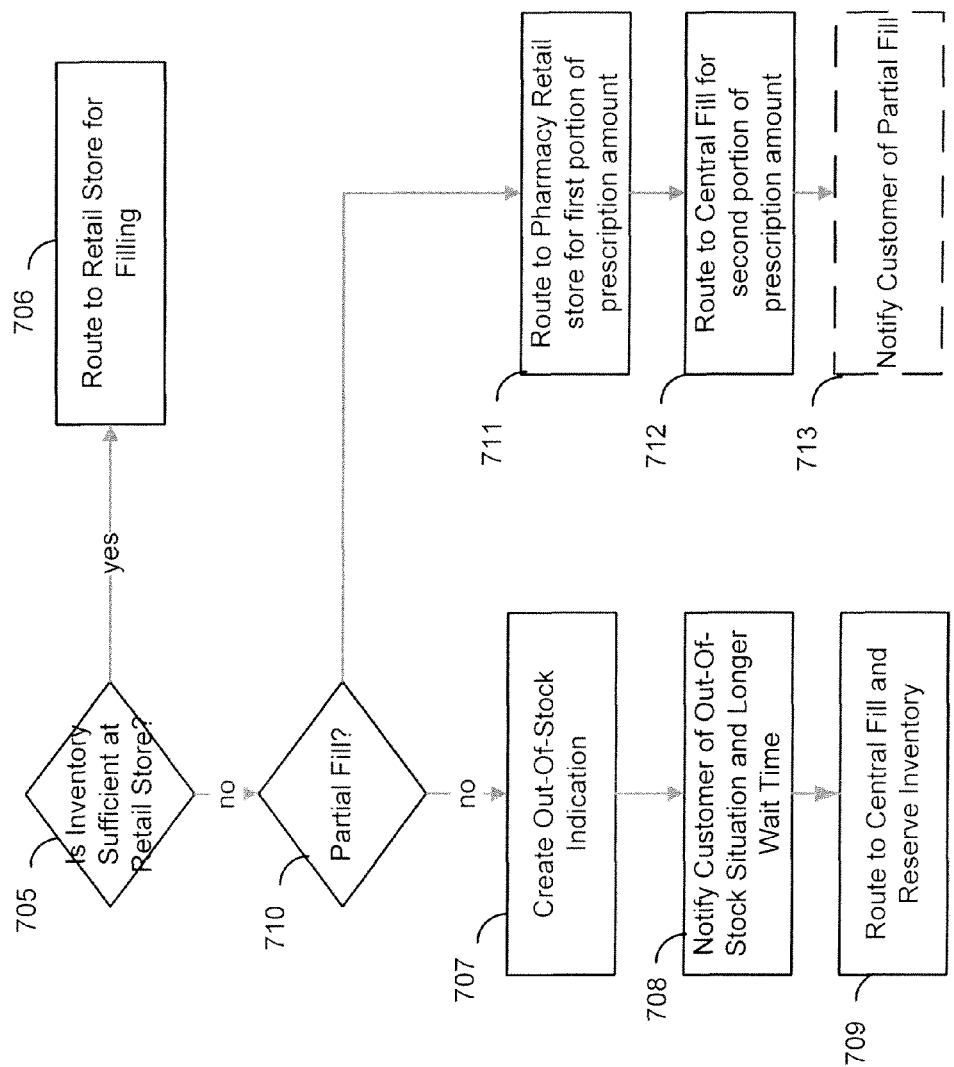
FIG. 7 illustrates an exemplary embodiment for providing partial prescription filling.

As discussed above, situations may exist when the pharmacy retail store contains sufficient inventory for only a portion a pharmacy product prescription and does not contain enough inventory to completely fill the prescription. A process embodiment for providing partial prescription filling is illustrated in FIG. 7, which shows modifications to the process of FIG. 6. In this embodiment, block 605 of FIG. 6 may include an inventory checking process to determine whether the pharmacy retail store inventory is sufficient to fill a portion of the prescription amount, shown as block 705 in FIG. 7. If the inventory is not sufficient, then an out-of-stock indication may be generated (block 707), a notification may be sent to a customer to inform the customer of the out-of-stock situation (block 708), and the prescription may be sent to the central fill for processing (block 709). If the pharmacy retail store inventory is sufficient to fill a portion of the prescription, then the prescription may be routed to the pharmacy retail store for physical preparation of a first portion of the prescription (block 711) and to the central fill for preparation of a second portion (block 712). A customer may optionally be notified of the partial fill situation (block 713).

In some embodiments, the partial fill determination of block 710 may include a number of intermediate determinations. For example, block 710 may be implemented only when a priority indication is associated with the electronic prescription. This indication may be placed on the prescription if a pharmacy product of the prescription is urgently needed (e.g., emergency medication). Moreover, an additional process may be to determine if a minimum partial fill quantity is available for the prescription product. This situation may arise when a minimum amount of pharmacy product is necessary for immediate release to a customer. Thus, block 710 may determine if a particular partial fill quantity is available at the pharmacy retail store. In some embodiments, an indication of a partial fill quantity may be associated with the prescription for use in block 710.

FIG. 4 illustrates a system embodiment including a central processing facility 430 in addition to a central filling facility 401. While the central filling facility 401 may be dedicated to physical preparation of a prescription once the prescription is information processed, the central processing facility 430 may be dedicated to information processing a raw electronic prescription order to produce the fill-ready, information processed prescription order used for physical filling. Generally, a central or regional processing facility may be implemented in a pharmacy network as further described in the aboveidentified application, entitled "System and Method of Information Processing of Raw Pharmacy Product Prescription in a Pharmacy Retail Network."

Figure 8:
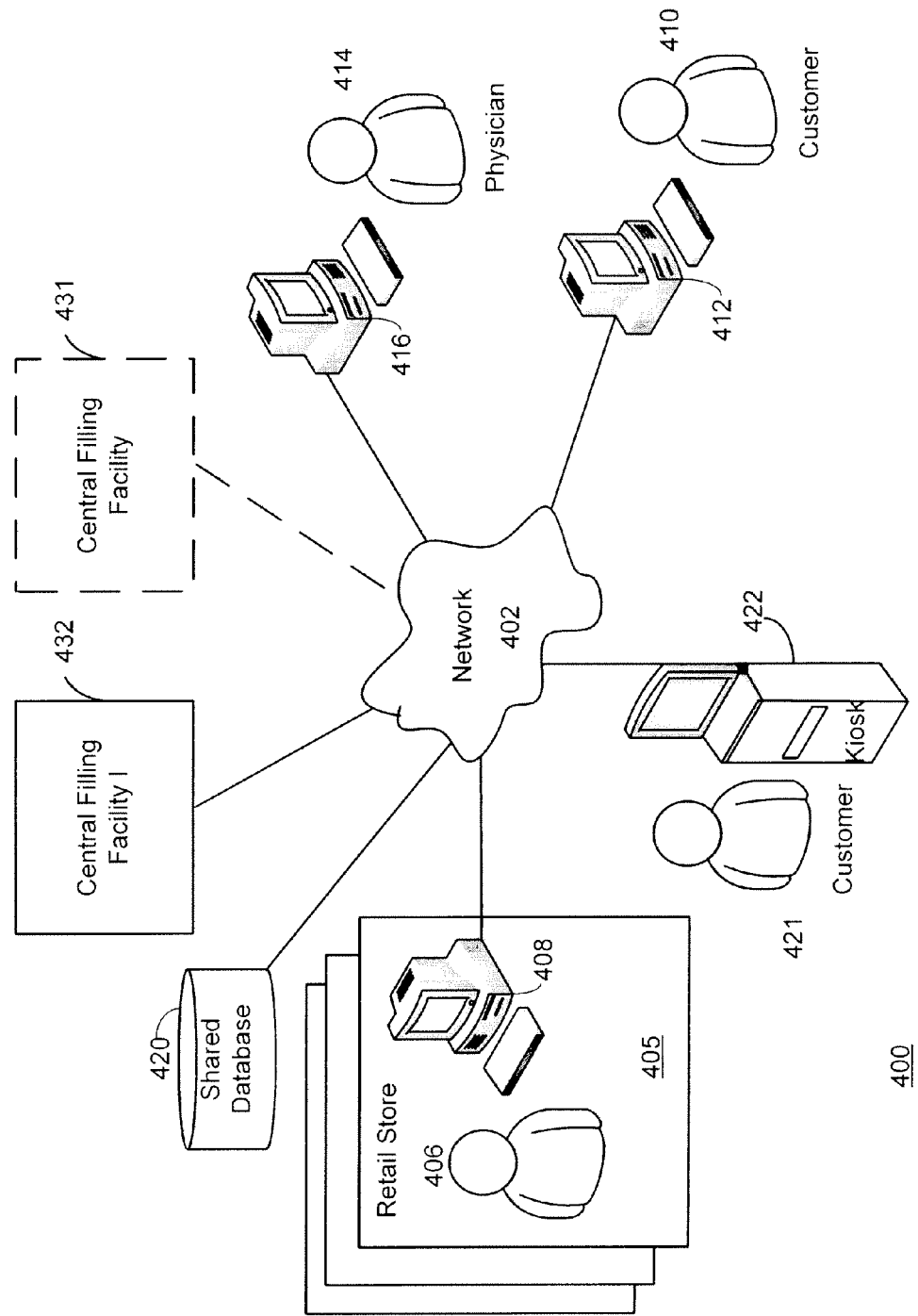
FIG. 8 illustrates an embodiment where more than one central facility may be used to prepare pharmacy products for electronic prescriptions of a pharmacy retail network.

Space limitations of a particular central filling facility may limit the size of the staff that operates the facility. Geographic proximity to the pharmacy retail stores may also be taken into account. Accordingly, FIG. 8 illustrates an embodiment where more than one central facility (431 and 432) may be used to prepare pharmacy products for electronic prescriptions of a pharmacy retail network. In this system, the processed electronic prescriptions may be routed to one or more central filling facilities connected to the network 402. The determination of routing between central fill facility 431 or 432 and a pharmacy retail store 405 may be similar to that described above. However, the decision to fill the processed electronic prescription at a first central filling facility 431 or a second central filling facility 432 may be based on parameters specific to the central filling facilities. In one embodiment, a processed prescription may be routed to one of the first or second central fill based on a workload of one or both facilities.

For example, a workload of the first and second facility may be determined and the processed prescription may be routed to the facility with less workload. This configuration may be used when the pharmacy network has a high volume of prescriptions that qualify for central fill (as opposed to retail store fills) where the central fills are normally operating near capacity. In this situation, the primary concern may be to ensure that none of the central filling facilities are overloaded with prescriptions.

Figure 9:
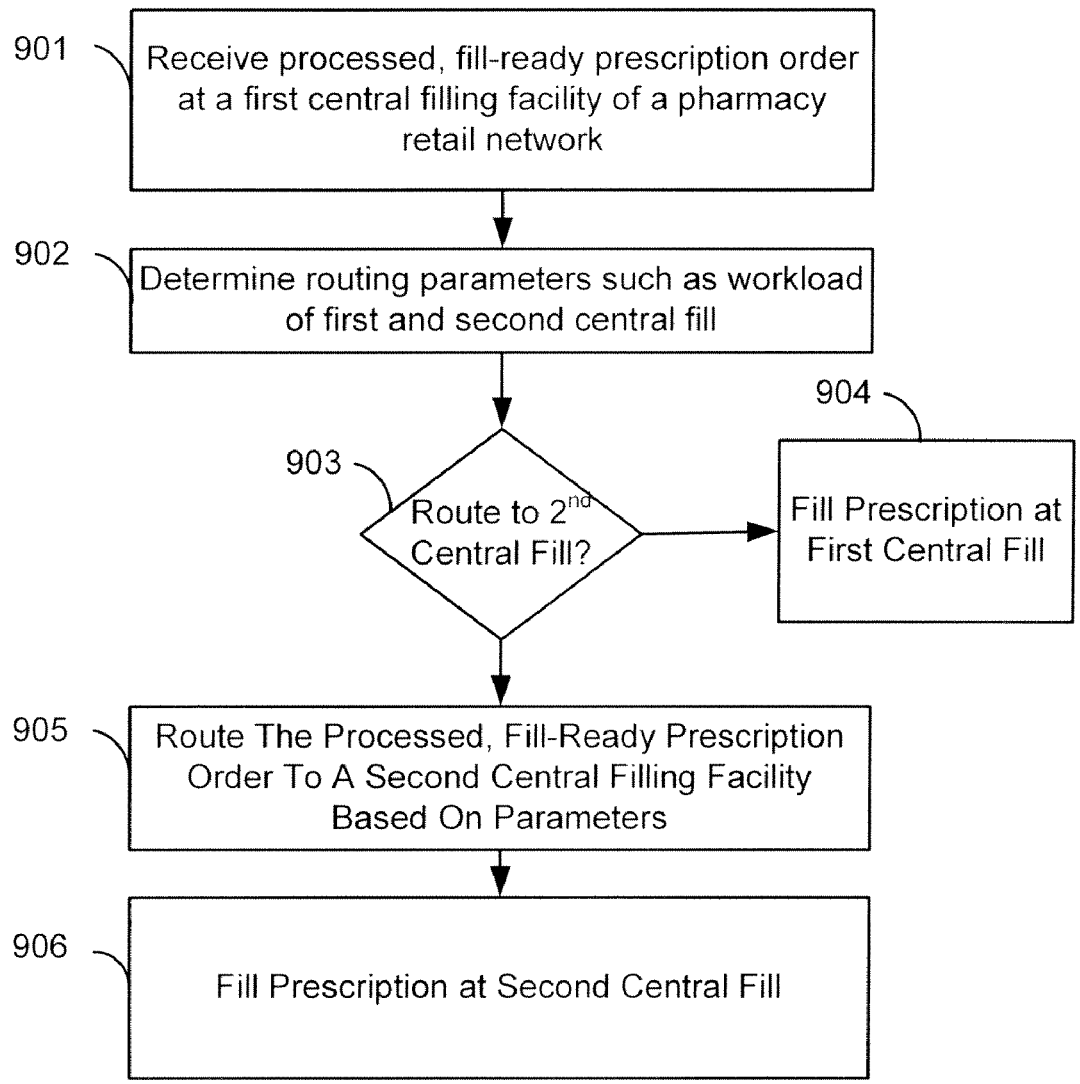
FIG. 9 illustrates an exemplary embodiment for routing prescription orders involving routing to a first central filling facility before a second central facility.

FIG. 9 illustrates an exemplary embodiment for routing prescription orders to one of two central filling facilities where all processed electronic prescriptions may be initially routed to a first central filling facility (block 901), such as central filling facility 431. The first central filling facility 431 may be configured to determine routing parameters (block 902), such as workload. Based on the routing parameters, a determination may be made as to where to fill the prescription (block 903). If the prescription is to be filled at the first central fill, then the first central fill may accept the prescription for physical filling (block 904). Otherwise, the prescription may be routed to a second central fill, such as central fill 432, at block 905 and filled at the second central fill 906.

In some embodiments the first central fill may be configured by default to fill all received electronic prescriptions unless its workload exceeds a threshold determined by and acted upon in the set of blocks 902 and 903. In particular, if the workload of the first facility is below a threshold as determined in block 902, then the processed prescription may be routed to the first central filling facility (block 904). If the workload of the first facility is above the threshold, the processed prescription may be routed to the second central filling facility (block 905). This configuration may be used when the pharmacy network generally operates at low central filling prescription volumes, thus waiting for the first central fill to reach a threshold capacity before routing additional orders to a second central fill. In one embodiment, the decision to route to a first or second central fill may be based on geography. For example, a first central fill may service a first area while the second central fill services a second area.

Figure 10:
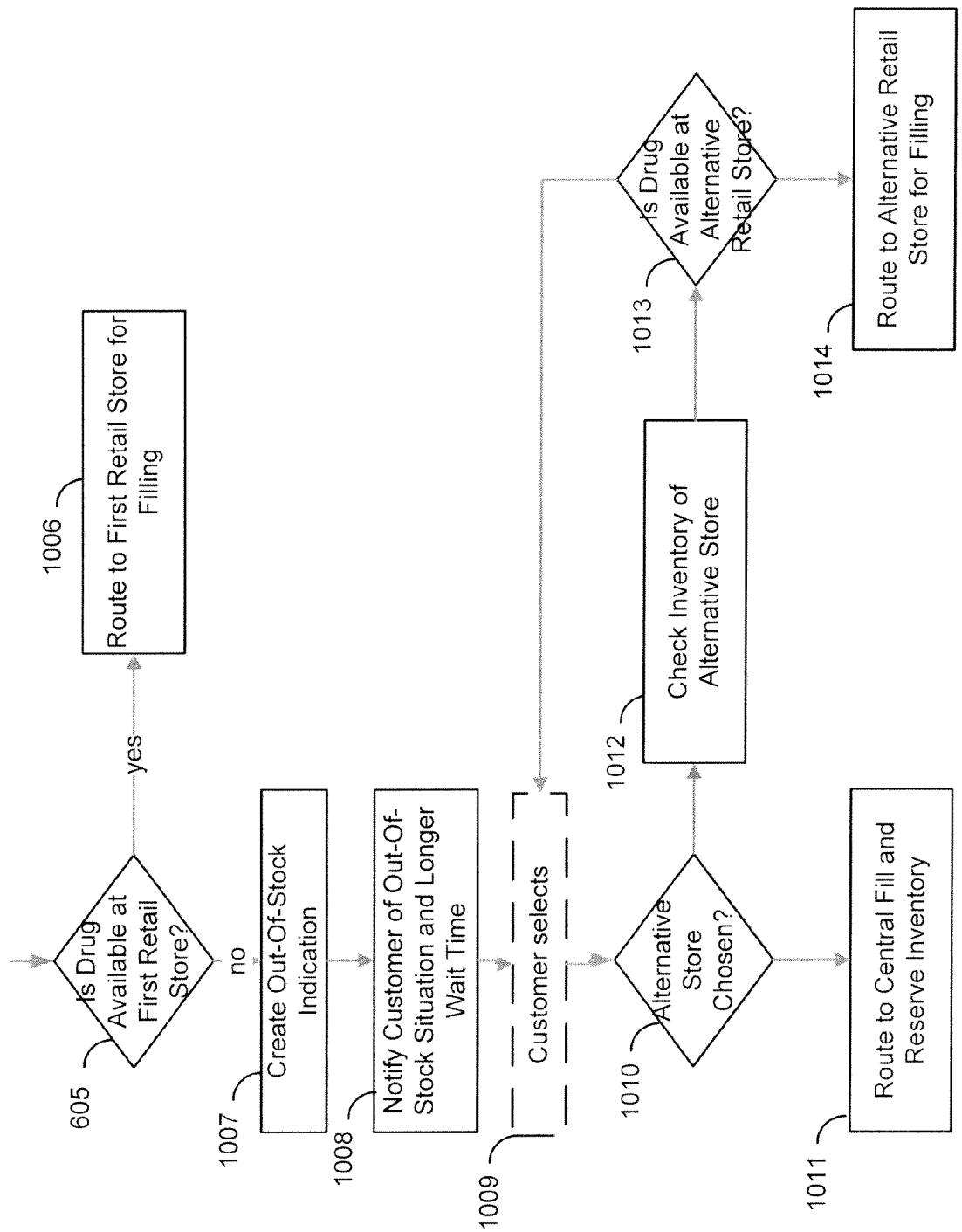
FIG. 10 illustrates an embodiment in which the processed prescription may be routed to one or more alternative pharmacy retail stores in the pharmacy retail network.

FIG. 10 illustrates an embodiment in which the processed prescription may be routed to an alternative pharmacy retail store in the pharmacy retail network. The process after block 605 of FIG. 6 may be illustrated in FIG. 10. If the pharmacy product is determined to be available at a first designated pharmacy retail store (block 605), then the processed prescription may be routed to that first pharmacy retail store (block 1006). If the pharmacy product is not available, an out-of-stock indication may be generated (block 1007) and a customer may be notified of the inventory problem (block 1008). In this embodiment, however, the customer may be given the opportunity to select an alternative store for filling and release of the prescription (block 1009). If an alternative store is not chosen (block 1010), then the prescription may be routed to the central filling center (block 1011) as described above. If an alternative store is chosen (block 1010), the inventory of pharmacy product for the prescription at the alternative store may be determined (block 1012). If the pharmacy product is available at the alternative store (block 1013) then the prescription may be routed to the alternative store (block 1014). If the pharmacy product is not available (block 1013), the system may prompt for another alternative store (block 1009) or simply route the prescription to the central filling facility (block 1011).

Figure 11:
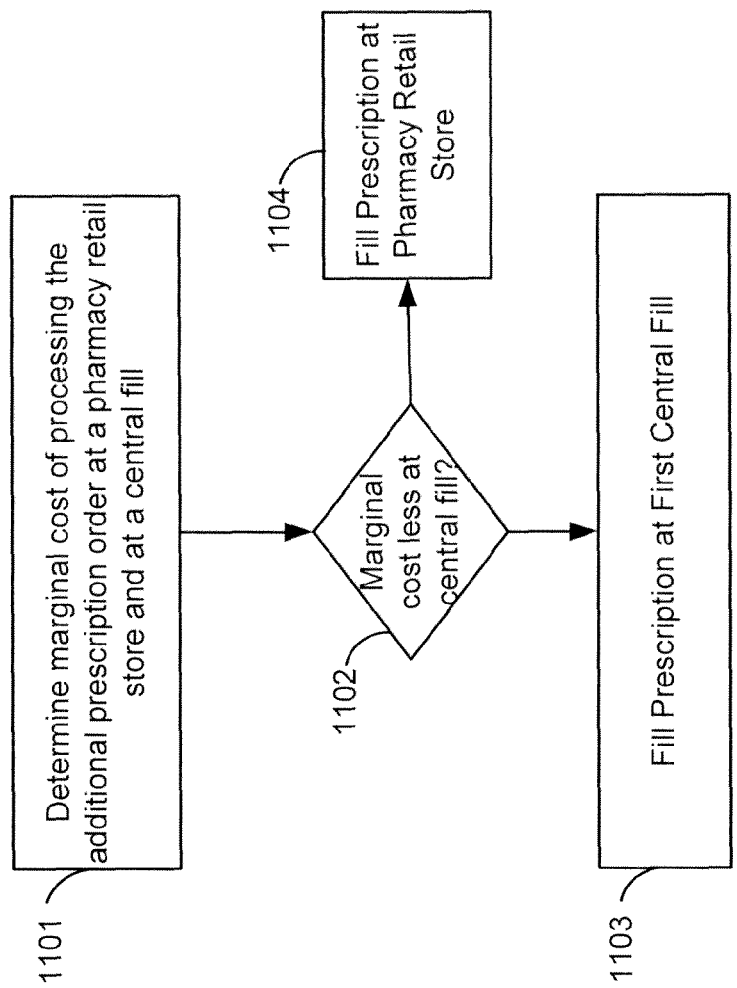
FIG. 11 illustrates an exemplary embodiment that routes the prescription order based on a difference in marginal cost to fill the prescription order between a pharmacy retail store and a central filling facility.

FIG. 11 illustrates a process embodiment that routes the prescription order based on a difference in marginal cost to fill the prescription order between a pharmacy retail store and a central filling facility. In this embodiment, an estimate of the marginal cost of filling a prescription order by the central fill and an estimate of the marginal cost of filling the prescription at a designated pharmacy retail store may be determined (block 1101). If the marginal cost of filling the prescription is less at the central fill than at the pharmacy retail store (block 1102), then the prescription may be routed to the central fill (block 1103). Otherwise, the prescription may be routed to the pharmacy retail store (block 11104). This embodiment may be used to send the bulk of all processed prescriptions in a pharmacy retail network to a central filling facility so long as the central filling facility is operating efficiently. Generally, a central filling facility may begin to become inefficient when it nears its operational capacity. In this case, the difference in cost to the pharmacy retail network between filling the prescription at a retail store versus the central fill may be small. In this situation, additional orders may be routed to pharmacy retail stores for filling. Alternatively, other parameters, such as those described above, may be used for routing.

A benefit of including a centralized, non-retail filling facility in a pharmacy retail network is that economies of scale may be used to more efficiently process a bulk quantity of prescriptions. However, simply including a centralized, non-retail filling facility in a pharmacy retail network may not necessarily provide increased operational efficiency without a prescription processing and routing system for determining when and how to route prescriptions to the central filling facility. The claimed method and system determines a set of parameters that may be used to determine opportune times to operate the filling process at one of a pharmacy retail store or a central filling facility. Accordingly, a plurality of information processed, fill-ready prescription orders may be received from a plurality of entities connected to the pharmacy retail network (e.g., pharmacy retail stores, kiosks, customers, physicians, etc.) and then routed based on the determined parameters. In this manner, prescriptions may be consolidated for processing at the central filling facility when appropriate or sent to pharmacy retail stores when necessary.

Economies of scale may be achieved in a number of ways. The central filling facility may be staffed with registered pharmacists and/or non-registered pharmacists to primarily fill prescriptions received from the network. Because the staff of registered pharmacists and/or non-registered pharmacists are concentrated on performing the primary task of prescription filling, less effort and time may be wasted on other distracting retail store related tasks. Moreover, a greater rate of prescription processing may be accomplished by consolidating the prescriptions for filling by specialists than by having retail stores individually perform filling as well customer relation management activities. Further, by using specialized bulk processing equipment at the central fill and aggregating the prescription orders at the central fill, costs of filling each prescription may be greatly reduced.

The invention claimed is:

1. A method of processing pharmacy product prescription orders within a network of pharmacy resources connected by a pharmacy computing network comprising:
   originating a raw electronic prescription order at a first pharmacy retail store, wherein the first pharmacy retail store releases pharmacy products directly to customers;
   information processing via a computer the raw electronic prescription order to produce a processed, fill-ready prescription order;
   computing a marginal cost of filling the fill-ready prescription order at a central filling facility;
      wherein the central filling facility is connected to the network of pharmacy resources via the pharmacy computing network; and
      wherein the central filling facility is a non-retail pharmacy resource separate and distinct from any pharmacy retail store;
   computing a marginal cost of filling the fill-ready prescription order at the first pharmacy retail store;
      wherein the first pharmacy retail store is connected to the network of pharmacy resources via the pharmacy computing network;
   routing the processed, fill-ready prescription order to the central filling facility when the computed marginal cost of filling the fill-ready prescription at the central filling facility is less than the computed marginal cost of filling the fill-ready prescription at the first pharmacy retail store;
   routing the processed, fill-ready prescription order to the first pharmacy retail store when the computed marginal cost of filling the fill-ready prescription at the first pharmacy retail store is less than the computed marginal cost of filling the fill-ready prescription at the central filling facility;
   physically preparing a type and quantity of a pharmacy product corresponding to the processed prescription order at the routed destination; and
   releasing the prepared pharmacy product to a customer.

2. The method of claim 1, further comprising information processing the raw electronic prescription order at a central information processing facility, wherein the central information processing facility is a non-retail pharmacy resource separate and distinct from any pharmacy retail store.

3. The method of claim 1, wherein releasing the pharmacy product to a customer comprises delivering the prepared prescription product to one of the first or a second pharmacy retail store for release to the customer.

4. The method of claim 1, wherein the information processed, fill-ready prescription order is routed to the central filling facility further based on at least one of the set of parameters including a pickup time of the electronic prescription order, an inventory level of the pharmacy product at the retail store, and an inventory level of the pharmacy product at the central filling facility.

5. The method of claim 1, wherein the information processed, fill-ready prescription order is routed to the central filling facility further based on a periodicity of the electronic prescription order.

6. The method of claim 1, further comprising reserving a quantity of pharmacy product as the routed destination based on the processed, fill-ready prescription order when routing the order to the central fill facility.

7. The method of claim 6, further comprising generating an alert indicating that an inventory level of a medication is low when the inventory level is insufficient to reserve the quantity of pharmacy product.

8. The method of claim 1, further comprising modifying the prescription to indicate a filling location of the pharmacy product as the central filling facility or a pharmacy retail store.

9. The method of claim 8, further comprising returning the pharmacy product based on the filling location indication.

10. The method of claim 8, further comprising returning a delivery-ready pharmacy product from a pharmacy retail store back to the central filling facility based on at least one of non-release of the pharmacy product, cancellation, or pharmacy product expiration.

11. The method of claim 1, further comprising routing the processed, fill-ready prescription order to one of the first computer of the first central filling facility, a first computer of a second central filling facility, or a computer of the first pharmacy retail store, wherein the first and second central filling facility are non-retail pharmacy resources separate and distinct from any pharmacy retail store.

12. The method of claim 11, further comprising routing the processed, fill-ready prescription order to one of the first computer of the first central filling facility or the first computer of the second central filling facility further based on an inventory level of the first and second central filling facilities.

13. The method of claim 11, further comprising routing the processed, fill-ready prescription order to one of the first computer of the first central filling facility or the first computer of the second central filling facility further based on a workload of the first and second central filling facilities, wherein the first and second central filling facility are non-retail pharmacy resources separate and distinct from any pharmacy retail store.

14. The method of claim 11, further comprising routing the processed, fill-ready prescription order to one of the first computer of the first central filling facility or the first computer of the second central filling facility further based on a proximity of the first pharmacy retail store to one of the first or second central filling facilities.

15. A method of processing pharmacy product prescription orders within a network of pharmacy resources connected by a pharmacy computing network comprising:
   connecting a plurality of pharmacy retail stores to a communication network, wherein each of the pharmacy retail stores physically releases pharmacy products directly to customers;
   connecting at least one non-retail central filling facility to the communication network wherein the central filling facility is a non-retail pharmacy resource separate and distinct from any pharmacy retail store;
   transmitting a plurality of electronic prescription orders over the communication network;
   computing a marginal cost of filling an electronic prescription order of the plurality of electronic prescription orders at the non-retail central filling facility;
   computing a marginal cost of filling the electronic prescription order at a first pharmacy retail store of the plurality of pharmacy retail stores;
   routing the electronic prescription order to the non-retail central filling facility when the computed marginal cost of filling the electronic prescription at the non-retail central filling facility is less than the computed marginal cost of filling the electronic prescription at the first pharmacy retail store of the plurality of pharmacy retail stores;

routing the electronic prescription order to the first pharmacy retail store when the computed marginal cost of filling the electronic prescription at the first pharmacy retail store is less than the computed marginal cost of filling the electronic prescription at the non-retail central filling facility;

physically preparing a type and quantity of a pharmacy product based on the routed electronic prescription order at the routed destination; and delivering the prepared pharmacy product to a first pharmacy retail store for release to a customer.

16. A system for processing pharmacy product prescription orders within a network of pharmacy resources connected by a pharmacy computing network comprising:

a first pharmacy computer at a first pharmacy retail store communicatively coupled to a network, wherein the first pharmacy retail store physically releases pharmacy products directly to customers;

a second pharmacy computer at a second pharmacy retail store communicatively coupled to the network, wherein the second pharmacy retail store physically releases pharmacy products directly to customers;

a central filling facility computer at a central filling facility coupled to the network and adapted to physically prepare a pharmacy product based on an electronic prescription order received via the network, wherein the central filling facility is a non-retail pharmacy resource separate and distinct from any pharmacy retail store; and a computing device communicatively coupled to the network and adapted to:

compute a marginal cost of filling the electronic prescription order at the central filling facility, and compute a marginal cost of filling the electronic prescription order at the first pharmacy retail store;

route the electronic prescription order to the central filling facility when the computed marginal cost of filling the electronic prescription at the central filling facility is less than the computed marginal cost of filling the electronic prescription at the first pharmacy retail store;

routing the electronic prescription order to the first pharmacy retail store when the computed marginal cost of filling the electronic prescription at the first pharmacy retail store is less than the computed marginal cost of filling the electronic prescription at the central filling facility.

17. The method of claim 16, wherein the electronic prescription order is routed to the central filling facility further based on a retail store inventory and a central filling facility inventory.

18. The system of claim 16, further comprising a second central filling facility computer at a second central filling facility coupled to the network and adapted to physically prepare a pharmacy product based on an electronic prescription order received via the network, wherein the second central filling facility is a non-retail pharmacy resource separate and distinct from any pharmacy retail store.

19. The system of claim 18, wherein the computing device is further adapted to route the electronic prescription order to one of the first central filling facility or the second central filling facility based on a workload of the first and second central filling facility or based on an inventory level of the first and second central filling facility.

20. The system of claim 19, further comprising bulk filling equipment disposed in the first and second central filling facilities.

* * * * *